United States Patent [19]

Vacca

[11] Patent Number: 5,380,295

[45] Date of Patent: Jan. 10, 1995

[54] DELIVERY APPARATUS WITH MECHANISM PREVENTING REARWARD MOVEMENT OF A PISTON DISPOSED THEREIN

[75] Inventor: Rita D. Vacca, Glendale, Mo.

[73] Assignee: Mallinckrodt Medical, Inc., St. Louis, Mo.

[21] Appl. No.: 988,267

[22] Filed: Dec. 14, 1992

[51] Int. Cl.6 .............................................. A61M 5/00
[52] U.S. Cl. ................................... 604/187; 604/199; 604/208; 604/218
[58] Field of Search ............... 604/110, 187, 218, 232, 604/207–209, 199

[56] References Cited

U.S. PATENT DOCUMENTS

| Re. 33,821 | 2/1992 | Banks | 604/110 |
|---|---|---|---|
| 2,875,761 | 3/1959 | Helmer et al. | |
| 4,367,738 | 1/1983 | Legendre et al. | |
| 4,391,273 | 7/1983 | Chiquiar-Arias | |
| 4,731,068 | 3/1988 | Hesse | 604/110 |
| 4,906,231 | 3/1990 | Young | 604/110 |
| 4,957,490 | 9/1990 | Byrne et al. | 604/197 |
| 4,978,339 | 12/1990 | Lebouze et al. | 604/110 |
| 4,995,869 | 2/1991 | McCarthy | 604/110 |
| 5,021,047 | 6/1991 | Movern | 604/110 |
| 5,095,914 | 3/1992 | Sarstedt | 128/765 |
| 5,135,514 | 8/1992 | Kimber | |
| 5,224,936 | 7/1993 | Gallager | 604/192 |

FOREIGN PATENT DOCUMENTS

| 0339954 | 11/1989 | European Pat. Off. | 604/110 |
|---|---|---|---|
| 0669910 | 4/1989 | Switzerland | 604/110 |
| 8900432 | 1/1989 | WIPO | 604/110 |
| 8909631 | 10/1989 | WIPO | 604/110 |
| 9011790 | 10/1990 | WIPO | 604/110 |

Primary Examiner—John D. Yasko
Attorney, Agent, or Firm—Rothwell, Figg, Ernst & Kurz

[57] ABSTRACT

A delivery apparatus in the form of a syringe assembly with a piston and including a mechanism for preventing withdrawal of the piston. The syringe is preferably prefilled and sterilized to provide a sterile syringe assembly with sterile contents. By preventing withdrawal of the piston, contact of the sterile contents with the exposed portion of the syringe barrel behind the piston and the consequent risk of contamination arising therefrom are avoided.

10 Claims, 5 Drawing Sheets

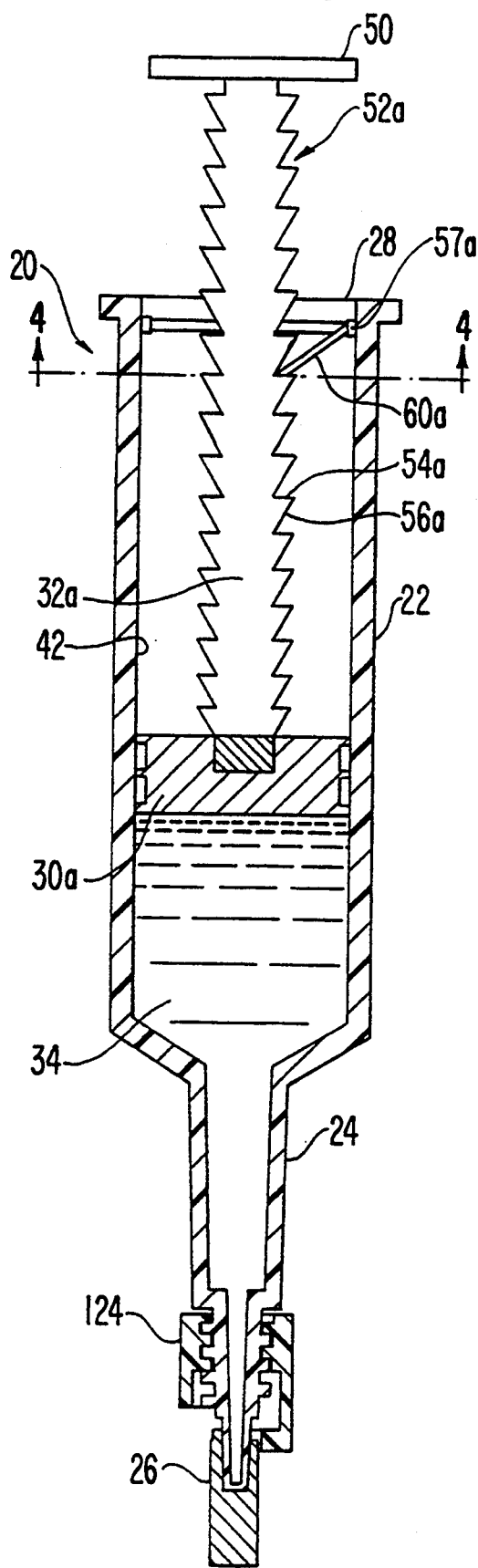
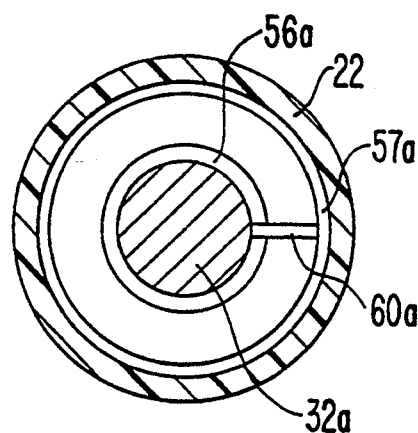

DELIVERY APPARATUS WITH MECHANISM PREVENTING REARWARD MOVEMENT OF A PISTON DISPOSED THEREIN

FIELD OF THE INVENTION

The present invention relates generally to delivery apparatus such as syringe assemblies that include a container portion in which a piston or plunger is slidably movable to expel fluid material disposed in the container portion. Specifically, the invention relates to such syringes in which the movement of the piston is restricted or limited.

DESCRIPTION OF THE PRIOR ART

Delivery apparatus in the form of syringes having a barrel portion with a delivery or nozzle end and an opposite open end that receives a piston or plunger are known in the prior art. In such devices, the piston is slidable in sealing engagement within the interior surface of the barrel and is movable in a forward direction towards the delivery end for expelling the syringe contents. The piston can also be withdrawn, i.e. moved in a reverse direction away from the delivery end, to perform various tasks, e.g. aspirating fluids which are to be disposed of or aspirating fluids into the syringe barrel for subsequent injection into a living subject, a catheter, etc.

It is further known in the art to manufacture prefilled, sterile delivery apparatus in the form of syringes that have been filled with a medical fluid, sealed to enclose the fluid within a storage volume formed by the syringe barrel, and sterilized to provide sterile syringe assemblies with sterile contents. For a disclosure of such prefilled syringes, see e.g. U.S. Pat. Nos. 4,628,969 and 4,718,463. Prefilled, sterile syringes of the type disclosed in the referenced patents are provided to hospitals or the like in a filled, sealed and sterile condition. To use the syringes, it is only necessary to break the seal of the delivery tip or nozzle, engage the piston with appropriate driving means and dispense the sterile fluid.

In using syringes of the above-described prefilled, sterile type, the interior of the syringe barrel which forms the storage volume and the fluid contents therein are sterile, but the exterior of the syringe, including the portion of the interior of the barrel disposed behind the piston, is usually not sterile. It is thus important that the piston not be withdrawn or retracted since such withdrawal allows contact between the sterile contents in the storage volume and the non-sterile area disposed behind the piston prior to such withdrawal, thus contaminating the sterile contents. As the piston is moved toward the delivery end of the barrel, an increasing area of this interior portion of the barrel behind the piston is exposed to non-sterile ambient conditions. Consequently, any withdrawal of the piston away from the delivery end of the barrel prior to fully expelling the barrel contents creates a significant contamination risk. This risk is caused by the sterile storage volume of the barrel having sterile contents therein communicating with the area of the barrel behind the piston that has been rendered non-sterile by the previous forward expelling movement of the piston. Accordingly, it is an object of the present invention to provide a delivery apparatus in which the aforementioned problems are overcome.

SUMMARY OF THE INVENTION

The present invention provides a delivery apparatus in the form of a prefilled, sterile syringe including a container portion with a piston configured to slidably engage the interior surface of the container portion in a sealing fashion, the container portion and the piston being provided with means for preventing withdrawal of the piston away from the delivery end of the container to maintain the sterility of the fluid contents disposed within the container portion.

Other features of the present invention will be apparent from the following description of the preferred embodiments taken in conjunction with the accompanying drawings wherein:

BRIEF DESCRIPTION OF THE DRAWINGS

FIG. 3 is a sectional view of a second embodiment of the present invention.

FIG. 4 is a sectional view taken along lines 4—4 of the embodiment shown in FIG. 3.

DETAILED DESCRIPTION OF THE PREFERRED EMBODIMENTS

Figure 1:
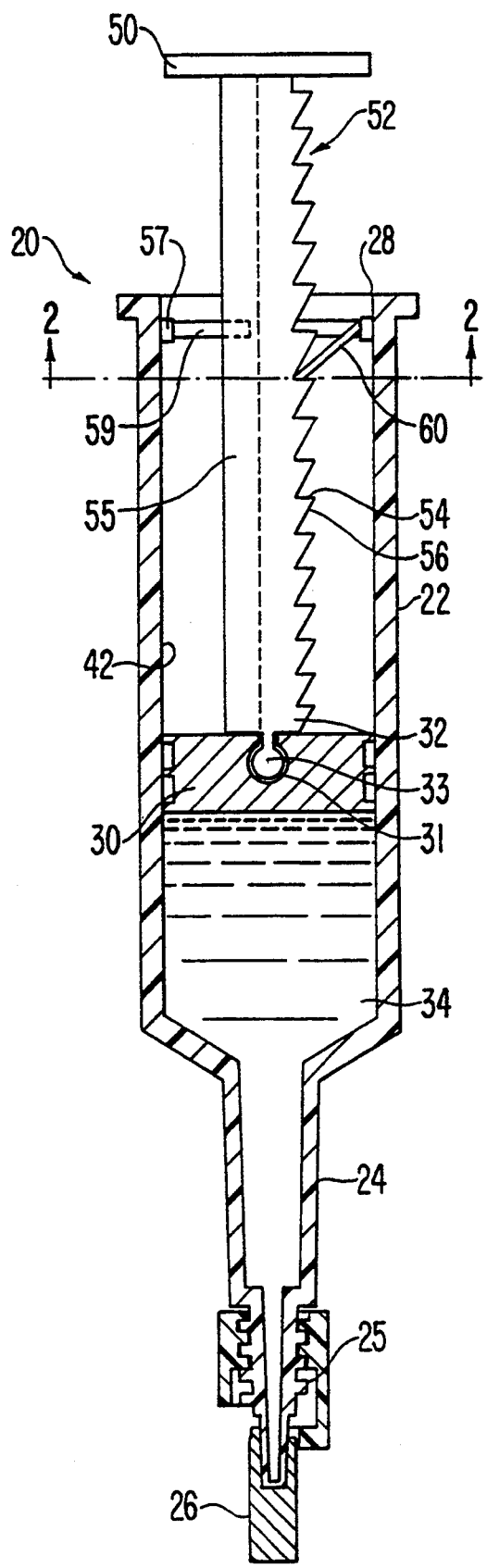
FIG. 1 is a sectional view of a delivery apparatus according to a first embodiment of the present invention.
Figure 2:
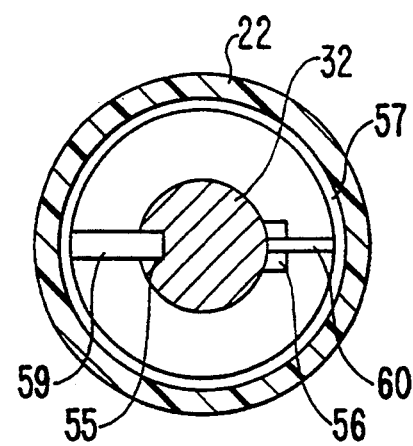
FIG. 2 is a sectional view taken along line 2—2 of the embodiment shown in FIG. 1.

Referring to the embodiment of the present invention shown in FIGS. 1 and 2, a delivery apparatus indicated generally at 20 is in the form of a syringe assembly including a housing portion or barrel 22 having a delivery end 24 and an open opposite end 28. A piston 30 is slidably engaged with the interior surface of housing portion 22 and together with the delivery end 24, which is sealed by a tip seal 26, forms a storage volume for the fluid contents 34. As used herein, fluid means a gas, liquid, or combinations thereof. In a preferred embodiment, the fluid is a medical fluid in that it contains a pharmaceutical media. While the housing portion 22 is depicted as being cylindrical, it is to be understood by those skilled in the art that such shape is exemplary and the use of "housing portion" or "barrel" herein encompasses both cylindrical and non-cylindrical syringe container portions, for example, but not limited to, square or triangular containers. The aforementioned storage volume is thus sealed at one end by the tip seal 26 and at the other end by the piston 30. The delivery end 24 is optionally designed to facilitate connection to additional medical apparatus and can include means, such as but not limited to the thread means 25 shown in FIG. 1, for the attachment of a luer connector of a conventional catheter (not shown). The syringe assembly also includes a push rod 32 for driving the piston 30, as will be discussed below.

In a preferred embodiment of the present invention, the syringe assembly 20 is a prefilled, sterile delivery apparatus which has been presterilized to provide a sterile syringe with sterile contents. Such prefilled, sterile syringes are similar to those disclosed in U.S. Pat. Nos. 4,628,969 and 4,718,463, assigned to the same assignee as the present application, the subject matter of which patents is incorporated herein by reference. These prefilled, sterile syringes are assembled, filled, sealed and sterilized to provide a sterile delivery device with sterile contents that can be shipped to hospitals and the like where they can be easily used to inject the contents during medical diagnostic and/or treatment procedures. It is desirable to provide such prefilled syringes in various sizes or volumes, i.e. different amounts of the fluid contents contained therein. It is also desirable to utilize a standard size syringe housing portion which can be filled to different levels to provide the aforementioned different volumes of fluid, as opposed to keeping many different size syringe housing portions on hand at the manufacturing site.

As a result, these prefilled, sterile syringes are often provided for end use in a partially filled condition, i.e. with the piston 30 disposed in the housing portion 22 so as to be displaced from the open end 28, as shown in FIG. 1. As stated above, while the fluid contents 34 contained within housing portion 22 between the piston 30 and the sealed delivery end 24 are sterile, the portion 42 of the interior of the housing 22 disposed behind the piston 30 will generally not be sterile. It is thus important that the sterile contents 34 not communicate with the aforementioned non-sterile portion 42 of housing portion 22. In many cases, it is desirable to prevent reverse movement of the piston, even initial withdrawal of the piston to aspirate the syringe.

Referring to the embodiment of FIGS. 1-2, the push rod 32 is provided with a thumb plate 50 and a series of ratchet-like teeth or projections 52 extending outward from a portion of the push rod 32. As mentioned above with respect to syringe housing portion 22, the push rod 32 is shown as cylindrical in cross-section, but it is to be understood that such shape is exemplary and that push rod 32 can be of a different shape. After placement of the piston within the barrel, the interior surface of housing portion 22 is provided with an insert member 57. The insert member 57 is shaped to fit in open end 28 of housing portion 22 and to be secured thereto by any suitable means as discussed below. A semi-flexible pawl or detent member 60 is carried by insert member 57 and is angled downward (toward the piston 30) from the insert member 57. The detent 60 is configured to engage the ratchet teeth 52 and is deflectable downward but its movement upward is restricted to a predetermined limit, as will be discussed below. The detent 60 is biased by appropriate means to extend to this limit and into engagement with the ratchet teeth 52. In a preferred embodiment, spring biasing means are employed, or alternatively, the detent 60 can be in the form of a leaf spring which can be deflected downward but not upward.

The insert member 57 also includes alignment means in the form of an alignment member 59 configured for engaging alignment means formed in push rod 32 as will be described below. Although the insert member 57 and detent 60 are shown disposed on the interior of housing portion 22 adjacent open end 28, those skilled in the art will recognize that such location is exemplary and that placement of insert member 57 and detent 60 elsewhere is within the scope of the present invention.

After the piston 30 has been placed in housing portion 22, the insert member 57 is positioned therein near the open end 28 thereof. Any suitable means can be used for securing insert member 57 to housing portion 22, including but not limited to adhesive, a press or snap-fit, or a threaded attachment. The push rod 32 is then inserted into housing portion 22 through open end 28 with the ratchet teeth 52 engaging the detent 60 as the push rod 32 moves downward. The push rod 32 includes alignment means in the form of a groove 55 in which the alignment member 59 of insert member 57 is placed as push rod 32 is inserted into housing portion 22. The cooperation of alignment member 59 with groove 55 insures that detent 60 engages ratchet teeth 52 to prevent piston withdrawal as will be discussed below. In the embodiment of FIG. 1, push rod 32 is inserted into housing portion 22 and is attached to piston 30 by a snap-fit. Specifically, the end of push rod 32 opposite finger plate 50 has a protrusion in the form of a knob 33 which is pressed into engagement with a recess 31 formed in piston 30. Engagement between the knob 33 and recess 31 can be accomplished without sufficient force to cause piston 30 to move forward while said engagement is being performed.

The ratchet teeth 52 each include a flat horizontal land surface 54 from which a slanted ramp surface 56 extends downward. The surfaces 54 and 56 engage the detent 60 in a known manner to allow movement of the push rod 32 in the aforementioned downward direction, but to prevent movement in the other direction. Downward movement of the piston 30 and push rod 32 into housing portion 22 is facilitated by placing alignment member 59 in groove 55 and depressing push rod 32. The alignment means insures that the detent 60 engages teeth 52. During downward movement of the push rod 32 towards delivery end 24, detent 60 rides up the slanted surface 56, but upon withdrawal of the push rod 32, detent 60 engages the flat surface 54 to prevent such withdrawal. Thus, the piston 30 and push rod 32 can be moved toward delivery end 24, but movement in the opposite direction is prevented.

As shown in the embodiment of FIGS. 1-2, the ratchet teeth 52 are formed on one side of the push rod 32 and engage the detent member 60 which extends from the insert member 57. Optionally, it is possible to form the teeth 52 as a plurality of spaced projections extending about the push rod. Further, the use of a non-circular push rod is also encompassed by the present invention, with the ratchet teeth or projections extending from a surface or surfaces thereof. The insert member 57 is positioned in the open end 28 of the syringe barrel 22 after the placement of piston 30, and preferably after the syringe has been subjected to a sterilization procedure, e.g. autoclaving, in which case the prefilled, sterile syringe assembly can be provided for end use with or without push rod 32 secured to piston 30. In the latter case, connection of push rod 32 to piston 30 would be performed by attending medical personnel. However, it is possible to assemble the push rod 32 in the housing portion 22 with the push rod 32 secured to piston 30 before sterilization since the semi-flexible detent 60, which is in engagement with the teeth 52, will permit limited upward movement of the piston 30 and push rod 32 to accommodate expansion of fluid 34 and/or piston 30 during the aforementioned autoclaving. In this case the prefilled, sterile syringe assembly would be provided for end use with the push rod 32 secured to piston 30.

A second embodiment of the present invention is shown in FIGS. 3–4 and includes a modified insert member 57a and a modified push rod 32a. The insert member 57a of this embodiment has extending therefrom a semi-flexible detent member 60a but does not have an alignment member because no alignment means are required with this embodiment. The push rod 32a has a series of coaxial ratchet teeth 52a formed along the length thereof, the teeth 52a extending completely around the push rod 32a as shown in FIG. 4. Because the teeth 52a extend all the way around push rod 32a, the detent 60a will engage the teeth 52a upon insertion of push rod 32a into housing portion 22 regardless of the relative angular positions of the push rod 32a and detent 60a. Rotation of push rod 32a to align the teeth 52a with the detent 60a is not required. Upon insertion of push rod 32a into housing portion 22, the one-way engagement between detent 60a and teeth 52a is like that of the first embodiment. Engagement of push rod 32a with piston 30a can be accomplished as in the first embodiment, or alternatively, can be facilitated by other means including but not limited to rotating a threaded extension of push rod 32a into a threaded recess formed in piston 30a. Rotation of push rod 32a while teeth 52a are engaged by detent 60a is possible to allow such engagement.

As with the first embodiment, the insert member 57a is positioned by suitable means in the open end 28 of the housing portion 22 after placement of piston 30a, and preferably after the syringe has been subjected to a sterilization procedure, e.g. autoclaving, although again it is possible to assemble the push rod 32a to the piston 30a before sterilization due to the semi-flexible nature of detent 60a which allows piston movement due to expansion during autoclaving. The prefilled, sterile syringe of the present invention thus has means for preventing withdrawal of the piston 30a, which withdrawal would lead to the aforementioned contamination risks arising from contact of the sterile fluid 34 with the portion 42 of the interior of housing portion 22.

Figure 5:
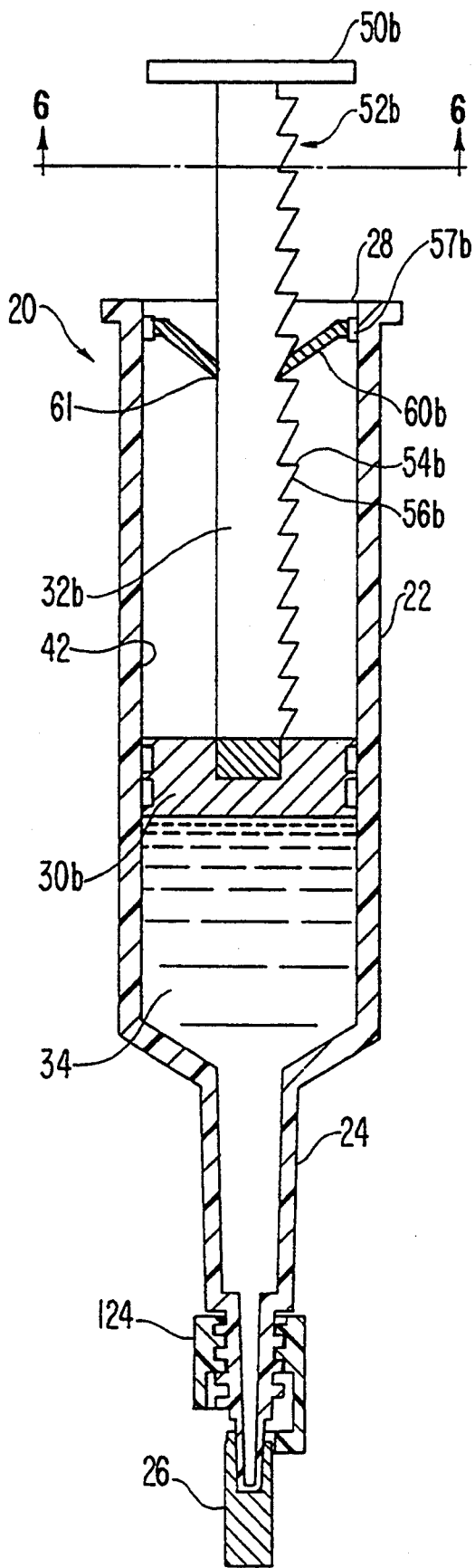
FIG. 5 is a sectional view of a third embodiment of the present invention.
Figure 6:
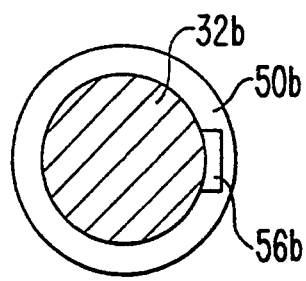
FIG. 6 is a sectional view taken along line 6—6 of the embodiment shown in FIG. 5.
Figure 7:
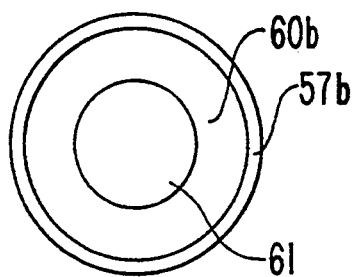
FIG. 7 is a top view of an insert and detent of the embodiment shown in FIGS. 5-6.

A third embodiment of the present invention is shown in FIGS. 5–7 and includes a further modified insert member 57b with a detent member 60b. The push rod in this embodiment is shown to have teeth 52b similar to the teeth 52 of the first embodiment. The insert member 57b has a semi-flexible detent member 60b which projects inward from an inner edge of member 57b. As seen in FIG. 7, detent member 60b is in the form of a continuous flat member extending downward from insert member 57 (toward piston 30b) with a central aperture 61 through which push rod 32b can be moved downward but not upward. It will be recognized that this shape of the detent 60b is exemplary and that detent 60b can be shaped otherwise so long as push rod 32b will engage said detent 60b at various angular positions of push rod 32b. The operation of the detent 60b and teeth 52b to prevent reverse movement of piston 30b is similar to that of the above embodiments. The push rod 32b can be connected to piston 30b by any suitable means, e.g. the snap-fit or threaded fit of the first two embodiments. The insert member 57b is positioned in housing portion 22 by suitable means discussed above with reference to the first two embodiments. The detent 60b is semi-flexible to allow limited movement of piston 30b during autoclaving, thus permitting attachment of push rod 32b to piston 30b prior to autoclaving as discussed above.

Another embodiment of the present invention (not shown) includes a housing portion 22 having secured thereto the insert member 57b of the embodiment of FIGS. 5–7 combined with the push rod 32a of the embodiment of FIGS. 3–4. The ratchet teeth 52a extend completely around push rod 32a as discussed above, and the insert member 57b has detent 60b in the form of a continuous member which surrounds push rod 32a upon insertion of the push rod into the housing portion 22. A benefit of this embodiment is that engagement between the detent 60b of insert member 57b and the teeth 52a of push rod 32a occurs completely around the push rod 32a, providing an enhanced engagement to further prevent reverse movement of the piston.

Figure 8:
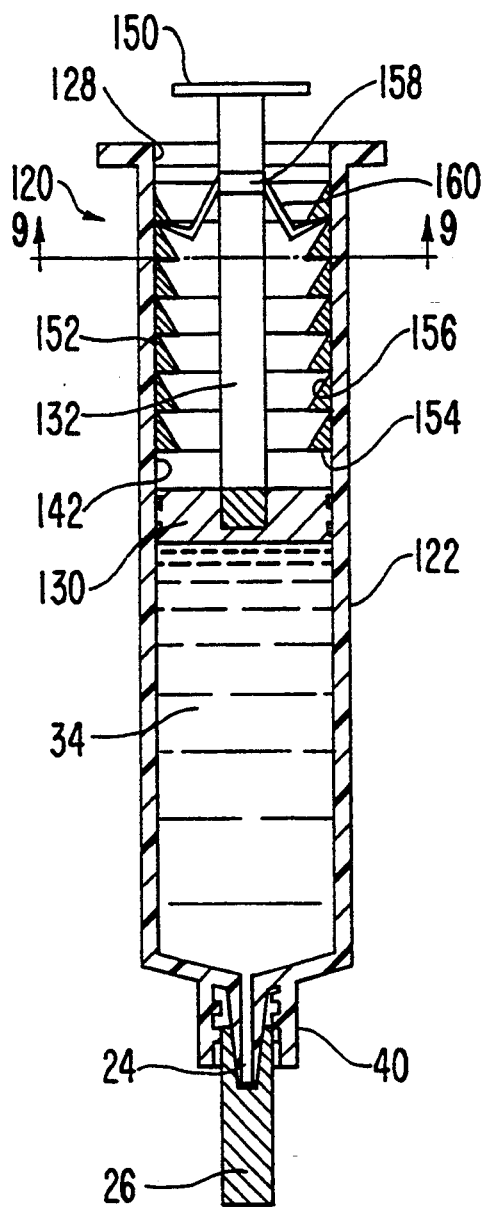
FIG. 8 is a sectional view of a fifth embodiment of the present invention.
Figure 9:
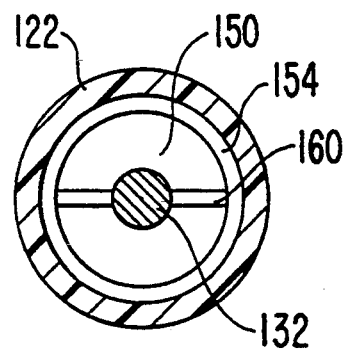
FIG. 9 is a sectional view taken along lines 9—9 of the embodiment shown in FIG. 8.
Figure 10:
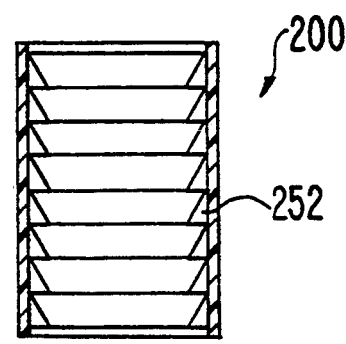
FIG. 10 is a sectional view of an insert member used in the embodiment of FIGS. 8-9.

A fifth embodiment of the present invention shown in FIGS. 8–9 includes a syringe with a housing portion 122 having an open end 128 and a delivery end 24, with the delivery end 24 including a sleeve or shroud 40 to facilitate attachment to additional medical apparatus (not shown), e.g. the luer connector of a conventional catheter. The housing portion 122 has provided on its upper interior surface a series of annular ratchet-like teeth 152. Each one of the ratchet teeth includes a horizontal land surface 154 from which a slanted ramp surface 156 extends upward. The ratchet teeth may, as shown in FIG. 10, alternatively be carried by an insert 200 configured and shaped to fit within the housing portion 222, or the housing portion of other embodiments. Insert 200 can be secured within housing portion 222 by any suitable means including but not limited to adhesive or a tight friction fit. The push rod 132 has a thumb plate 150 at an upper end and at its lower end is connected to piston 130 by any suitable means, e.g. the snap-fit or threaded fit of the previously described embodiments. A collar-like member 158 is secured to the push rod 132 adjacent the upper end below thumb plate 150, and a pair of pawl-like detents 160 are secured to and extend from the collar member 158. Those skilled in the art will recognize that it is within the scope of the present invention to utilize other than two detents, e.g. one, three, or more detents. It is likewise within the scope of the present invention to position the collar member 158 on the push rod 132 other than as shown or, alternatively, to secure the detents 160 directly to the push rod, 132 or, as a further alternative, to form the detents 160 integrally with the push rod 132.

The detents 160 engage the ratchet teeth 152 so as to allow downward movement of the push rod 132, but to prevent movement thereof in an opposite direction in a manner similar to that described with respect to the embodiment of FIG. 1. The detents 160 are biased, preferably spring biased, into engagement with the ratchet teeth 152. As in the case of the embodiments of FIGS. 1–4, the syringe 120 is partially filled with sterile fluid 34, and assembly of the push rod 132 with the piston 30 is preferably performed prior to the sterilization procedure, although as in the embodiments of FIGS. 1–7 the detent 160 is semi-flexible to allow assembly of the push rod 132 to piston 30 before sterilization as discussed above. The combination of the ratchet teeth 152 provided on the interior of the barrel wall and the detents 160 carried by the push rod 132 prevents withdrawal of the piston 130, which withdrawal will cause the sterile fluid 34 to come into contact with the portion 142 of the interior of the housing portion 122 and present a significant contamination risk.

Figure 11:
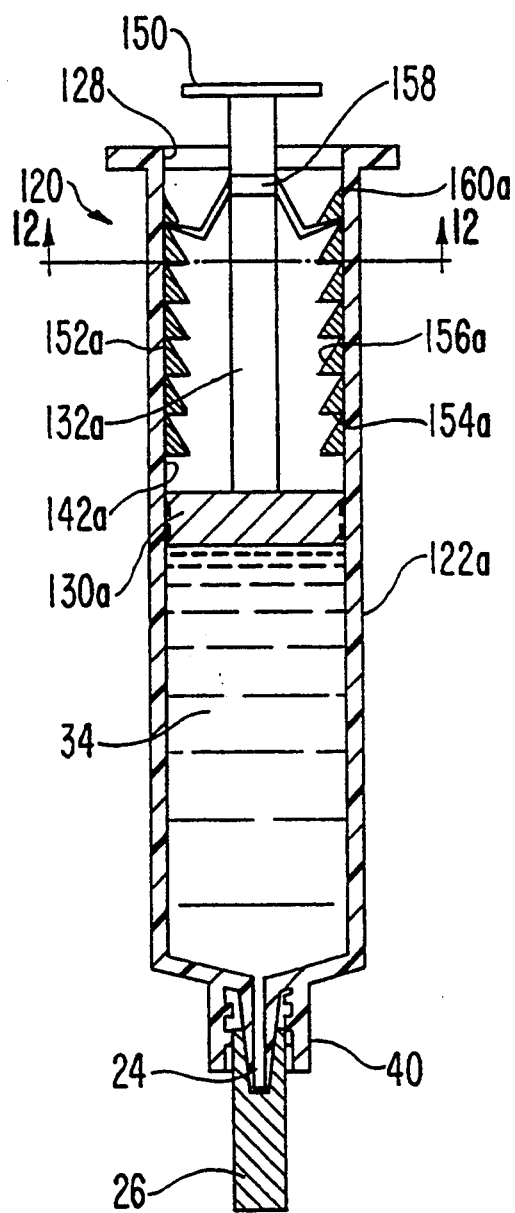
FIG. 11 is a sectional view of a sixth embodiment of the present invention.
Figure 12:
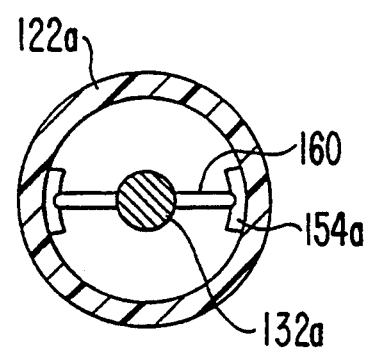
FIG. 12 is a sectional view taken along lines 12—12 of the embodiment shown in FIG. 11.

A sixth embodiment of the present invention is shown in FIGS. 11-12 in the form of a syringe including a housing portion 122a and a piston 130a with a push rod 132a attached to the piston 130a by any suitable means as discussed above with reference to the above embodiments. The interior of housing portion 122a is provided with a series of ratchet teeth 152a which, as described above regarding FIG. 10, can be provided on a separate insert such as member 200. The ratchet teeth 152a do not cover the entire interior surface of housing portion 122a as they do in the embodiment of FIGS. 8-9. The push rod 132a has a detent member 160a secured thereto for engaging the ratchet teeth 152a to prevent reverse movement of push rod 132a and piston 130a. The detent 160a is in the form of a continuous flat member extending away from push rod 132a and will engage ratchet teeth 152a of housing portion 122a as described above, i.e. to allow movement of push rod 132a and piston 130a towards the delivery end to expel fluid 34 but to prevent movement in the opposite direction.

Further embodiments of the present invention include a syringe with the housing portion 122 of FIGS. 8-9, which is covered with ratchet teeth, and the push rod 132a having a continuous detent 160a of FIGS. 11-12. In addition, it is possible to have an embodiment of the present invention in the form of syringe having the housing portion 122a of FIGS. 11-12, which is partially covered with ratchet teeth 152a, and the push rod 132 and detents 160 of FIGS. 8-10. In the embodiment of FIGS. 11-12, the attachment of push rod 132a to piston 130a, accomplished by suitable means such as the threaded coupling shown, permanently aligns the detent 160a with ratchet teeth 152a.

While the present invention and the embodiments presented herein have been set forth and described in detail for the purposes of making a full and complete disclosure of the subject matter thereof, the disclosure herein presented is not intended to be limiting in any way with respect to the true scope of this invention as the same is set forth in the appended claims.

What is claimed is:

1. A delivery apparatus comprising:
   a container portion having a delivery end and an opposite open end adapted to receive a piston;
   a piston adapted to be positioned in said container portion so as to be sealingly slidable against an interior surface of said container portion;
   a push rod connectible to said piston for moving said piston within said container portion along said interior surface in a forward direction towards said delivery end to expel material contained within said container portion; and
   means for continuously preventing movement of said piston in the reverse direction away from said delivery end including at least one semi-flexible detent member extending away from the interior of said container portion, said at least one detent member arranged to engage a series of projections formed on said push rod by moving into and out of engagement with consecutive projections of said series of projections, said means for preventing movement of the piston in the reverse direction permitting said piston to move a predetermined limited distance in said reverse direction, said predetermined distance being selected so as to allow the filled, sealed delivery apparatus to be sterilized with the push rod connected to the piston by accommodating slight movement of the piston during said sterilization, whereby said at least one detent member and said projections permit movement of said push rod and piston towards said delivery end but prevent movement of same away from said delivery end beyond said predetermined limited distance.

2. A delivery apparatus as claimed in claim 1, wherein said at least one detent member is carried by an insert member attached to said interior surface of the container portion.

3. A delivery apparatus as claimed in claim 1, including alignment means for aligning said at least one detent member with said series of projections.

4. A prefilled, sterile delivery apparatus comprising:
   a container portion having a sealed delivery end and a piston positioned in said barrel so as to be sealingly slidable against an interior surface of said barrel;
   a storage volume formed in said barrel, said storage volume containing fluid;
   means connected to said piston for moving said piston within said container portion along said interior surface in a forward direction towards said delivery end to expel said fluid contained within said container portion; and
   means for preventing movement of said piston in a reverse direction away from said delivery end;
   wherein the entire apparatus is presterilized to provide a sterile delivery apparatus with sterile contents.

5. A prefilled, sterile delivery apparatus as claimed in claim 4 wherein said means for moving the piston towards said delivery end includes a push rod connected to said piston.

6. A delivery apparatus as claimed in claim 5, wherein said means for preventing movement of said piston in a reverse direction away from said delivery end includes a detent member secured to and extending away from the interior of said container portion configured to engage a series of projections formed on said push rod, whereby said detent and said projections permit movement of said push rod and piston towards said delivery end but prevent movement of same away from said delivery end.

7. A delivery apparatus as claimed in claim 6, including alignment means for aligning said at least one detent member with said series of projections.

8. A method of producing a prefilled, sterile delivery apparatus, the method comprising the steps of:
   forming a container having a sealed delivery tip and a hollow interior, said container having an open end disposed opposite said sealed delivery tip;
   providing the container with means for preventing movement of a piston positioned in the container beyond a predetermined limited distance in a direction away from said sealed delivery tip and towards said open opposite end, said means for preventing piston movement cooperating with means for driving the piston towards said delivery tip to prevent movement of the piston in said direction beyond said predetermined limited;
   filling said container with a predetermined quantity of medical fluid and sealing said open end with a piston to form a sealed container having medical fluid therein; and sterilizing the filled, sealed container with the piston disposed therein to produce a prefilled, sterile delivery apparatus.

9. A method according to claim 8, wherein said sterilizing step is carried out by autoclaving the filled, sealed container.

10. A method of producing a prefilled, sterile delivery apparatus, the method comprising the steps of:

forming a container having a sealed delivery tip and a hollow interior, said container having an open end disposed opposite said sealed delivery tip;

providing the container with means for preventing movement of a piston positioned in the container in a direction away from said sealed delivery tip and towards said open opposite end, said means for preventing piston movement cooperating with means for driving the piston towards said delivery tip to prevent movement of the piston in said direction;

filling said container with a predetermined quantity of medical fluid and sealing said open end with a piston to form a sealed container having medical fluid therein; and sterilizing the filled, sealed container with the piston disposed therein to produce a prefilled, sterile delivery apparatus.

* * * * *